(12) United States Patent
Kolvenbach et al.

(10) Patent No.: US 10,875,012 B2
(45) Date of Patent: Dec. 29, 2020

(54) PROCESS FOR THE PREPARATION OF MOLYBDENUM DISULFIDE NANOPARTICLES SUPPORTED ON TITANIA

(71) Applicant: SHELL OIL COMPANY, Houston, TX (US)

(72) Inventors: Robin Kolvenbach, Garching (DE); Marcello Stefano Rigutto, Amsterdam (NL); Thomas Weber, Amsterdam (NL); Lennart Van Haandel, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/316,684

(22) PCT Filed: Jul. 13, 2016

(86) PCT No.: PCT/EP2016/066656
§ 371 (c)(1),
(2) Date: Jan. 10, 2019

(87) PCT Pub. No.: WO2018/010784
PCT Pub. Date: Jan. 18, 2018

(65) Prior Publication Data
US 2019/0151830 A1    May 23, 2019

(51) Int. Cl.
*B01J 27/051*    (2006.01)
*B01J 37/03*    (2006.01)
(Continued)

(52) U.S. Cl.
CPC ........... *B01J 27/051* (2013.01); *B01J 21/063* (2013.01); *B01J 27/0515* (2013.01);
(Continued)

(58) Field of Classification Search
CPC ...... B01J 27/051; B01J 35/1019; B01J 37/16; B01J 27/0515; B01J 35/0013;
(Continued)

(56) References Cited

U.S. PATENT DOCUMENTS

| | | | | |
|---|---|---|---|---|
| 8,048,399 B2* | 11/2011 | Hayashi | ............... | C01G 23/047 423/610 |
| 2006/0039850 A1* | 2/2006 | Jun | ...................... | C09K 11/883 423/561.1 |
| 2011/0172483 A1 | 7/2011 | Choi et al. | | |

FOREIGN PATENT DOCUMENTS

| | | | | |
|---|---|---|---|---|
| EP | 2606972 A1 * | 6/2013 | ............. | C10G 45/08 |
| RU | 2297878 C2 | 4/2007 | | |

OTHER PUBLICATIONS

Cassaignon et al., Journal of Physics and Chemistry of Solids 68 (2007) 695-700. (Year: 2007).*

(Continued)

*Primary Examiner* — Ali Z Fadhel
(74) *Attorney, Agent, or Firm* — Charles W. Stewart (57) ABSTRACT

The invention relates to a process for the preparation of nanoparticles of $MoS_2$ supported on $TiO_2$ wherein the preparation is performed by reductive coprecipitation using aqueous solutions containing Ti and Mo precursor salts, and wherein $MoS_2$ may be non-promoted or Co-promoted. Further, the invention relates to the use of said nanoparticles as hydrodesulfurization catalysts.

14 Claims, 10 Drawing Sheets

(51) Int. Cl.
| | |
|---|---|
| B01J 21/06 | (2006.01) |
| B01J 37/16 | (2006.01) |
| C10G 45/08 | (2006.01) |
| B01J 35/10 | (2006.01) |
| B01J 35/00 | (2006.01) |
| C07C 1/32 | (2006.01) |

(52) U.S. Cl.
CPC ....... *B01J 35/0013* (2013.01); *B01J 35/1019* (2013.01); *B01J 37/033* (2013.01); *B01J 37/035* (2013.01); *B01J 37/16* (2013.01); *C07C 1/322* (2013.01); *C10G 45/08* (2013.01); *B01J 2523/00* (2013.01); *C07C 2521/06* (2013.01); *C07C 2527/051* (2013.01); *C07C 2601/16* (2017.05); *C10G 2300/202* (2013.01)

(58) Field of Classification Search
CPC ...... B01J 21/063; B01J 37/035; B01J 37/033; B01J 2523/00; B01J 37/082; B01J 35/023; C10G 45/08; C10G 2300/202; C07C 1/322; C07C 2527/051; C07C 2521/06; C07C 2601/16
See application file for complete search history.

(56) References Cited

OTHER PUBLICATIONS

International Search Report and Written Opinion received for PCT Patent Application No. PCT/EP2016/066656, dated Apr. 18, 2017, 8 pages.
Maity et al., "TiO2—ZrO2 Mixed Oxide as a Support for Hydrotreating Catalyst", Catalysis Letters, vol. 72, Issue No. 1-2, Jan. 1, 2001, pp. 115-119, XP055358785.
Xie et al., "The In Situ Controllable Loading of Ultrafine Noble Metal Particles on Titania." Journal of American Chemical Society, vol. 131, Issue No. 19, Apr. 23, 2009, pp. 6648-6649.
Ramirez et al., "The Role of Titania In Supported Mo, Como, Nimo, and Niw Hydrodesulfurization Catalysts: Analysis of Past and New Evidences", Catalysis Today, vol. 98, Issue No. 1-2, Nov. 24, 2004, pp. 19-30.
Coulier et al., "TiO2-Supported Mo Model Catalysts: Ti as Promoter for Thiophene HDS?", Catalysis Letters, vol. 79, Issue No. 1-4, Apr. 2002, pp. 149-155.
Zheng et al., "A General Synthetic Strategy for Oxide-Supported Metal Nanoparticle Catalysts", Journal of American Chemical Society, vol. 128, Issue No. 44, Oct. 13, 2006, pp. 14278-14280.
Blanco et al., "Novel One Step Synthesis of Porous Supported Catalysts by Activated-Carbon Templating", Advanced Materials, vol. 18, Issue No. 9, Jul. 2006, pp. 1162-1165.
White et al. "Supported Metal Nanoparticles on Porous Materials, Methods and Applications", Chemical Society Reviews, vol. 38, Issue No. 2, 2009, pp. 481-494.
Wang et al., "One-step Room-temperature Synthesis of [Al]MCM-41 Materials for the Catalytic Conversion of Phenylglyoxal to Ethylmandelate", ChemCatChem, vol. 5, Issue No. 12, Dec. 2013, pp. 3889-3896.
Sprung et al., "Methane Steam Reforming over a Ni/NiAl2O4 Model Catalyst—Kinetics", ChemCatChem, vol. 6, May 23, 2014, pp. 1969-1982.
Campelo et al., "Sustainable Preparation of Supported Metal Nanoparticles and their Applications in Catalysis", ChemSusChem. vol. 2, Issue No. 1, Jan. 20, 2009, pp. 18-45.
Golunski et al., "Low-Temperature Redox Activity in Co-precipitated Catalysts: A Comparison Between Gold and Platinum-group Metals", Catalysis Today, vol. 72, Issue No. 1-2, Feb. 15, 2002, pp. 107-113.

Ho et al. "Preparation and Photocatalytic Behavior of MoS2 and WS2 Nanocluster Sensitized TiO2", Langmuir, vol. 20, Issue No. 14, 2004, pp. 5865-5869.
Chhowalla et al., "The Chemistry of Two-dimensional Layered Transition Metal Dichalcogenide Nanosheets", Nat Chem., vol. 5, Issue No. 4, Apr. 2013, pp. 263-275.
Prins, "Handbook of Heterogeneous Catalysis", vol. 6, 2008, pp. 2696-2718.
Breysse et al., "Recent Studies on the Preparation, Activation and Design of Active Phases and Supports of Hydrotreating Catalysts", Catalysis Today, vol. 130, Issue No. 1, Jan. 15, 2008, pp. 3-13.
Ng et al., "Molybdena on Titania: Preparation and Characterization by Raman and Fourier Transform Infrared Spectroscopy", Journal of Catalysis, vol. 92, 1985, pp. 340-354.
Ramirez et al., "Hydrodesulphurization Activity and Characterization of Sulphided Molybdenum and Cobalt-molybdenum Catalysts : Comparison of Alumina-, Silica-Alumina- and Titania-Supported Catalysts", Applied Catalysis, vol. 52, Issue No. 1, 1989, pp. 211-224.
Dzwigaj et al., "New Generation of Titanium Dioxide Support for Hydrodesulfurization", Applied Catalysis B: Environmental, vol. 41, Issue No. 1-2, Mar. 10, 2003, pp. 181-191.
Toledo-Antonio et al., "Highly Active CoMos Phase on Titania Nanotubes as New Hydrodesulfurization Catalysts", Applied Catalysis B: Environmental, vol. 90, Issue No. 1-2, 2009, pp. 213-223.
Guevara et al., "Effect of TiO2-Al2O3 Sol-Gel Supports on the Superficial Ni and Mo Species in Oxidized and Sulfided State and Their Performance on Dibenzothiophene Hydrodesulfurization", Catalysis Letters, vol. 126, Issue No. 3-4, Dec. 2008, pp. 268-274.
Barrera et al., "Dibenzothiophene Hydrodesulfurization Activity of MoS2 Supported in Sol-Gel ZrO2—TiO2 Mixed Oxides", Petroleum science and technology, vol. 22, Issue No. 1-2, Jan. 2, 2004, pp. 87-101.
Zhang et al., "Hydrodesulfurization of Resid Fluid Catalytic Cracking Diesel Oil Over TiO2—SiO2 Supported Catalysts",EnergyFuels, vol. 20, Issue No. 6, Sep. 23, 2006, pp. 2293- 2298.
Huang et al., "Ti-Modified Alumina Supports Prepared by Sol-Gel Method Used for Deep HDS Catalysts", Catalysis Today, vol. 131, Issue No. 1-4, Feb. 2008, pp. 314-321.
Wei et al., "Hydrodesulfurization Activity of NiMo/TiO2-Al2O3 catalysts", Applied Catalysis A: General, vol. 167, Issue No. 1, Feb. 5, 1998, pp. 39-48.
Nguyen et al., "One Pot Sol-Gel Preparation for Efficient Cobalt-Molybdenum-Titania Hydrotreating Catalysts", ChemCatChem, vol. 4, Sep. 27, 2012, pp. 2112-2120.
Di Paola et al., "Photocatalytic Activity of Nanocrystalline TiO2 (Brookite, Rutile and Brookite-based) Powders Prepared by Thermohydrolysis of TiCl4 in Aqueous Chloride Solutions", Colloids and Surfaces A: Physicochemical Engineering Aspects, vol. 317, Issue No. 1-3, Mar. 20, 2008, pp. 366-376.
Cassaignon et al., From TiCl3 to TiO2 Nanoparticles (Anatase, Brookite and Rutile): Thermohydrolysis and Oxidation in Aqueous Medium, Journal of Physics and Chemistry of Solids, vol. 68, Issue No. 5-6, May-Jun. 2007, pp. 695-700.
Wang et al., "Hydrolysis of TiCl(4): initial steps in the production of TiO(2), Hydrolysis of TiCl(4): initial steps in the production of TiO(2)", Journal of Physical Chemistry A, vol. 114, Issue No. 28, Jul. 1, 2010, pp. 7561-7570.
Weber et al., "Structure of Amorphous MoS3", Journal of Physical Chemistry, vol. 99, Issue No. 22, Jun. 1995, pp. 9194-9200.
Afanasiev et al., "Surfactant-Assisted Synthesis of Highly Dispersed Molybdenum Sulfide", Chemistry of Materials, vol. 11, Issue No. 11, 1999, pp. 3216-3219.
Muijsers et al. "Sulfidation Study of Molybdenum Oxide Using MoO3/SiO2/Si(100) Model Catalysts and MO3-IV Sulfur Cluster Compounds", Journal of Catalysis, vol. 157, Issue No. 2, Dec. 1995, pp. 698-705.

\* cited by examiner

PROCESS FOR THE PREPARATION OF MOLYBDENUM DISULFIDE NANOPARTICLES SUPPORTED ON TITANIA

CROSS REFERENCE TO RELATED APPLICATIONS

This is a national stage application of International Application No. PCT/EP2016/066656, filed 13 Jul. 2016.

FIELD OF THE INVENTION

The present invention relates to a process for the preparation of titania ($TiO_2$)-supported molybdenum disulfide ($MoS_2$) nanoparticles and to the use of said nanoparticles obtained by said process as hydrodesulphurization catalysts.

BACKGROUND OF THE INVENTION

The synthesis of industrial heterogeneous catalysts, composed of highly dispersed active nanoparticles on a porous support, usually involves multiple steps.[1] Typically, the support is prepared and shaped first and subsequently loaded with the desired metal salt precursors. Several steps of drying, calcination and activation are then required to obtain the catalytically active phase, each exhibiting some inherent drawbacks. For example, during drying the precursor may migrate and agglomerate at the pore mouth. Calcination can lead to incorporation of the precursor into the support and activation may lead to initial sintering of metal nanoparticles, resulting in a loss of catalytic activity and/or selectivity.[1-2] The development of synthetic routes that involve fewer steps is thus not only economically attractive, but it may also lead to a higher degree of control over materials properties.

Several one-step methodologies have been reported for the synthesis of heterogeneous catalysts containing noble[3] or non-noble[3b,4] metal nanoparticles. However, despite their simplified preparation, calcination and/or reduction may still be required to obtain the catalyst in its active state. Reduction by $H_2$ or other reducing agents such as $NaBH_4$ can be circumvented if the support facilitates reduction directly. Redox active supports (or their precursors) such as $CeO_2$ and $TiO_2$ are capable of reducing noble metal salts in solution to obtain supported metallic nanoparticles directly.[5] Such an approach has not yet been demonstrated for non-noble metals, although the deposition of small amounts of $MS_2$ (M=Mo, W) on $TiO_2$ by photoreduction suggests that a similar approach may work for transition metal disulfides (TMS).[6]

TMS are an important class of materials that have attracted interest in a variety of fields such as catalysis and energy storage.[7] In particular, they are broadly applied in refineries to catalyze the removal of heteroatoms (S, N, O, Ni, V, etc.) from oil. Hydrotreating (HDT) catalysts are typically composed of Co or Ni promoted molybdenum disulfide ($MoS_2$) nanoparticles supported on $\gamma$-$Al_2O_3$.[8] Several researchers have reported that $TiO_2$ as a support improves intrinsic hydrodesulfurization (HDS) performance by a factor of four to five.[9] Nevertheless, practical applications of $TiO_2$ as support in HDS catalysts are limited by its maximum Mo-loading, which is constrained by the lower surface area compared with $Al_2O_3$.[9a,10]

Several strategies were proposed to overcome the low Mo-capacity of $TiO_2$. These strategies include the synthesis of high surface area $TiO_2$[10], mixed supports of $TiO_2$ with other metal oxides ($ZrO_2$, $Al_2O_3$ and $SiO_2$)[11], and the synthesis of $TiO_2$-coated $Al_2O_3$.[12] Despite the higher Mo-loadings accommodated by these supports, in all cases Co and Mo were added by post-impregnation. Recently, Nguyen et al. reported a single step synthesis of $TiO_2$ supported Co—Mo oxide HDT catalyst precursors by sol-gel method.[13] By this approach, the Mo-loading could be varied up to 30 wt %. A drawback of this method was that part of the Mo was incorporated in the support and remained unsulfided. Consequently, the samples prepared by sol-gel method were less active than impregnated samples with the same Mo-loading.

The aim of the present invention is to find a process which provides an improvement over the processes described in the prior art.

SUMMARY OF THE INVENTION

It has now been found that molybdenum disulfide nanoparticles supported on titania can be synthesized from aqueous solutions containing Ti and Mo precursor salts by an in situ redox reaction.

Accordingly, the present invention relates to a method for the preparation of nanoparticles of $MoS_2$ supported on $TiO_2$ wherein the preparation is performed by reductive coprecipitation (RCP) using aqueous solutions containing Ti and Mo precursor salts, and wherein $MoS_2$ is non-promoted or Co-promoted. By using the direct synthesis process according to the invention non-promoted and Co-promoted $MoS_2$ nanoparticles supported on $TiO_2$ ($MoS_2/TiO_2$ and Co—$MoS_2/TiO_2$, respectively) are produced.

The process according to the invention involves a redox reaction between $Ti^{3+}$ and $MoS_4^{2-}$ in aqueous solution and proceeds readily under mild conditions. It is believed that this is the first example of simultaneous formation of support and metal sulfide nanoparticles in a single step. Furthermore, unlike the sol-gel method, no evidence was found that co-precipitation may lead to encapsulation of active $MoS_2$ particles by the support.

The catalysts produced by the process according to the invention (i.e. the non-promoted and/or Co-promoted $MoS_2$ nanoparticles) proved to be highly active in the hydrodesulfurization (HDS) of dibenzothiophene (DBT) under mild conditions (40 bar, 245° C.), even in the absence of Co. The remarkable activity of the unpromoted catalyst, which is competitive with a commercial alumina supported Co—Mo reference, can be attributed to an increased hydrogenation activity. This suggests that Ti ($TiO_2$) may act as a promoter for $MoS_2$ in hydrogenation reactions. The as-synthesized catalysts were characterized by transmission electron microscopy (TEM), energy-dispersive X-ray spectroscopy (EDX), X-ray diffraction (XRD), X-ray fluorescence (XRF) and X-ray photoelectron spectroscopy (XPS).

It is a further object of the present invention to provide for the use of molybdenum disulfide nanoparticles supported on titania as produced by the coprecipitation process of the present invention as hydrodesulfurization catalysts, wherein the molybdenum disulfide is non-promoted or Co-promoted.

DETAILED DESCRIPTION OF THE INVENTION

The present invention relates to a process for the production of molybdenum disulfide nanoparticles supported on titania from aqueous solutions containing Ti and Mo precursor salts by an in situ redox reaction. The synthesis involves a redox process between $Ti^{3+}$ and $MoS_4^{2-}$, which proceeds readily under mild conditions in aqueous solution.

In an embodiment of the invention, preparation of the nanoparticles is in a single step directly from a solution of the respective metal salts $TiCl_3$ and $(NH_4)_2MoS_4$.

In another embodiment of the invention, preparation of the nanoparticles is in two steps from a dispersion of $TiO_{2-x}$ support precursor in a solution of $(NH_4)_2MoS_4$, wherein the $TiO_{2-x}$ support precursor is prepared prior to introduction of the $(NH_4)_2MoS_4$ salt.

Accordingly, catalysts were made in a single step, yielding amorphous catalysts with high Mo content, or in two steps to obtain $MoS_2$ supported on well-defined $TiO_2$ with lower Mo content. Catalysts obtained via single step reductive coprecipitation were highly active in the HDS of dibenzothiophene (DBT), exceeding the activity of an alumina-supported Co—Mo reference. In contrast to alumina-supported catalysts, the addition of Co as promoter did not enhance the catalytic activity of $MoS_2/TiO_2$ to the same extent (+30%) as for alumina-supported Co—Mo catalysts. Instead, a change in selectivity towards hydrogenolysis products at the expense of hydrogenation products was observed. It is suggested that Ti may act as a promoter for $MoS_2$ in hydrogenation reactions.

In an embodiment of the invention, the Ti and Mo precursor salts are $TiCl_3$ and $(NH_4)_2MoS_4$, respectively.

Preferably, the preparation is in a single step directly from a solution of the respective metal salts $TiCl_3$ and $(NH_4)_2MoS_4$.

Figure 1:
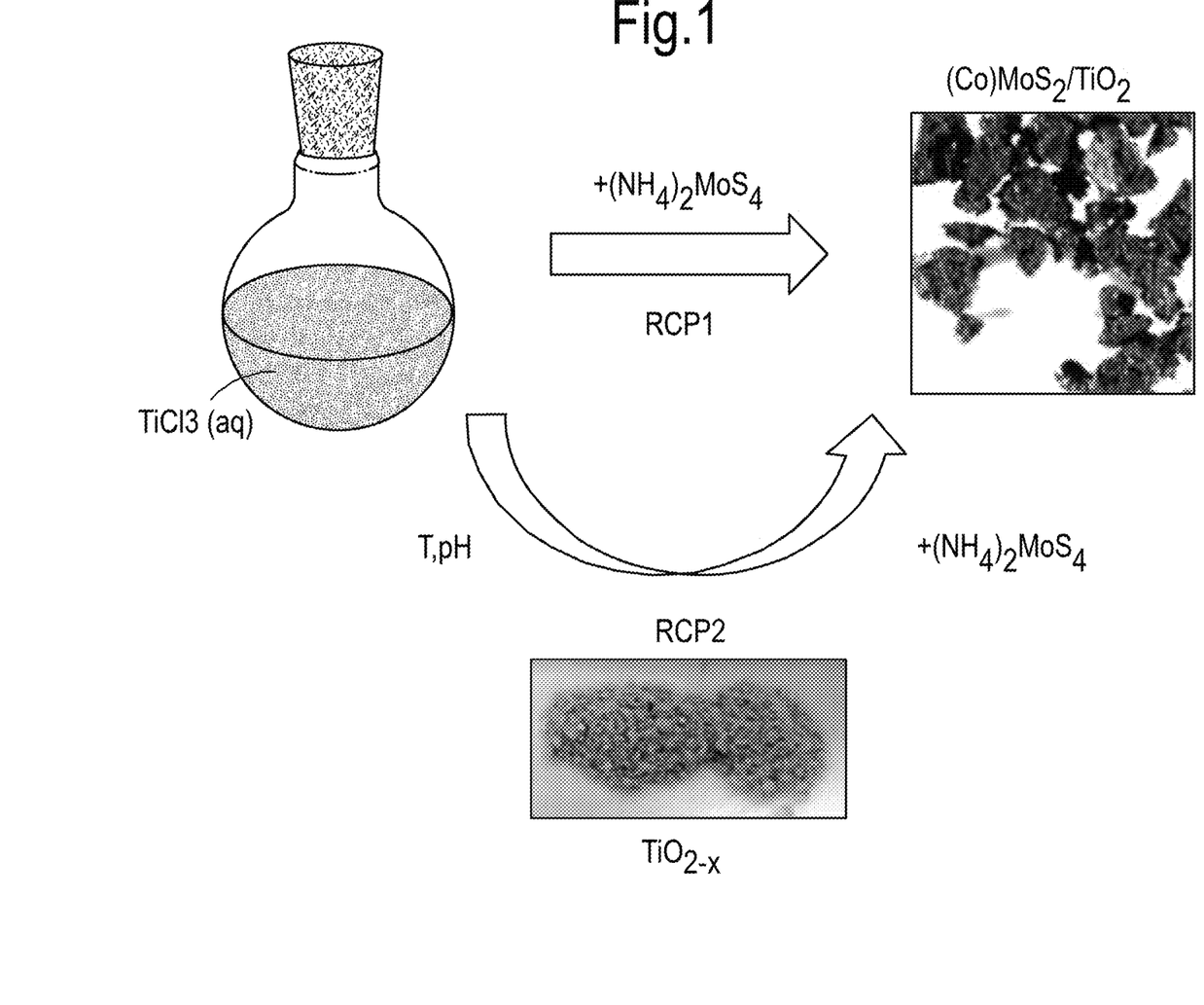
FIG. 1: Schematic representation of the one-step (RCP1) and two-step (RCP2) reductive coprecipitation processes. While in RCP1 the product forms directly in an aqueous solution of the precursor salts, RCP2 involves preparation of $TiO_{2-x}$ and subsequent loading with $MoS_2$.

Results and Discussion $TiO_2$ supported $MoS_2$ catalysts were synthesized from aqueous solutions of $(NH_4)_2MoS_4$ and $TiCl_3$ by reductive co-precipitation (RCP). The method involves hydrolysis and oxidation of $TiCl_3$ and simultaneous reduction and decomposition of $(NH_4)_2MoS_4$ to $MoS_2$ (FIG. 1).

The involved redox process is formally described by the following half-reactions:

$$2Ti^{3+} \rightarrow 2Ti^{4+} + 2e^- \quad (1)$$

$$Mo^{6+} + 2e^- \rightarrow Mo^{4+} \quad (2)$$

Figure 6:
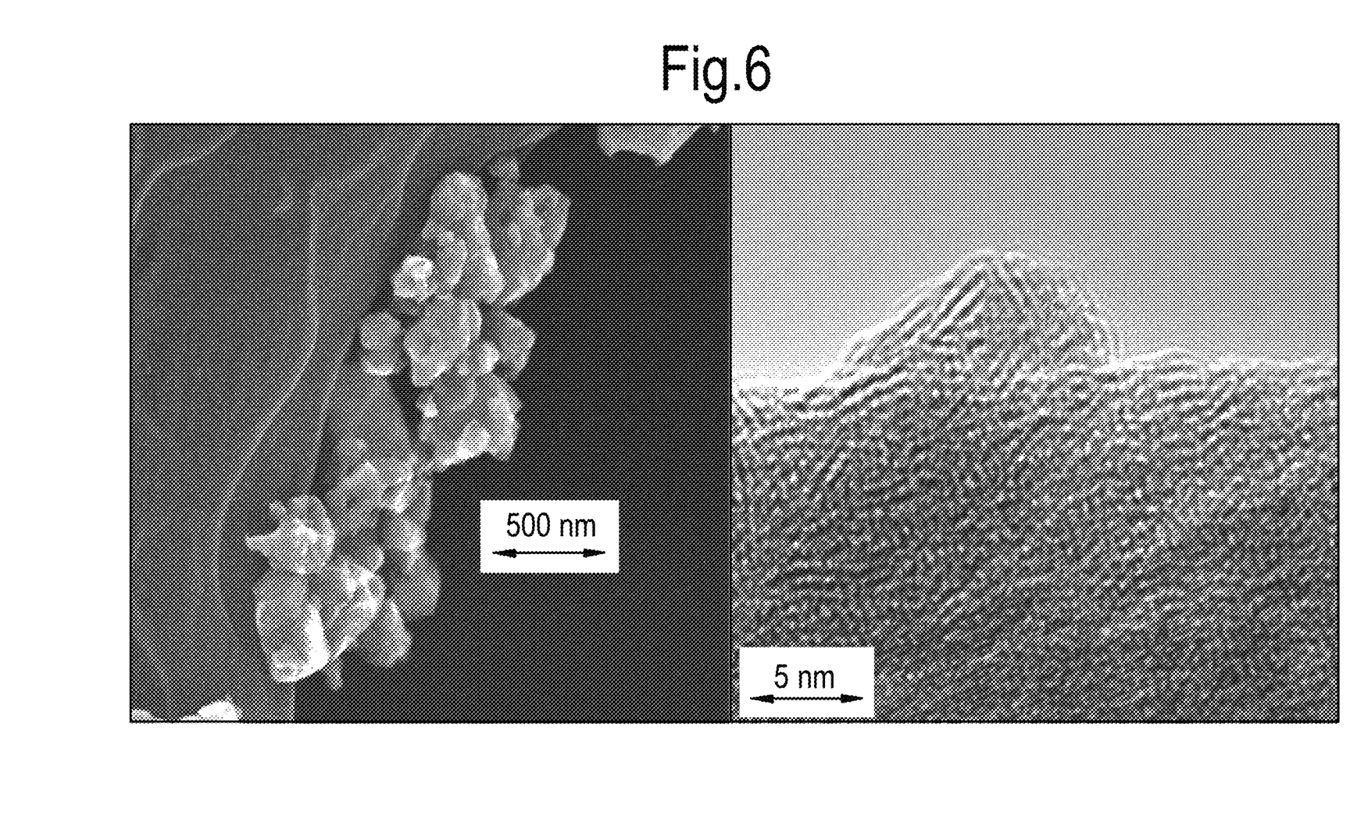
FIG. 6: secondary electron TEM image (left) and HR-TEM image (right) of sample $MoS_2$-sol.

Genesis of the supported catalysts is likely an interplay between redox, hydrolysis and condensation reactions. $TiCl_3$ is hydrolyzed and subsequently condensates to form a gel-like structure, similar to the early stage of $TiO_2$ synthesis from $TiCl_4$.[14] Simultaneously, $Ti^{3+}$ is oxidized by $MoS_4^{2-}$ yielding $MoS_2$. It was found that reduction of $MoS_4^{2-}$ proceeds readily under mild acidic or neutral conditions. Indeed, $MoS_2$ spontaneously precipitates upon addition of a neutral solution of $Ti^{3+}$, chelated by nitrilotriacetic acid, to a neutral solution of $(NH_4)_2MoS_4$ (see Supporting Information and FIG. 6). However, under alkaline conditions $Ti^{3+}$ is rapidly oxidized by water or hydroxyl anions to $Ti^{4+}$. Consequently, $MoS_2$ does not form under these conditions.

Under acidic conditions, the reduction of $MoS_4^{2-}$ by $Ti^{3+}$ is in competition with its hydrolysis to $MoS_3$ (Equation 3), an amorphous $Mo^{IV}$ solid, which cannot take part in the redox process anymore.[15]

$$Mo^{IV}S_4^{2-} + 2H_3O^+ \rightarrow Mo^{IV}S_3 + H_2S + 2H_2O \quad (3)$$

The formation of $MoS_3$ was suppressed by addition of a chelating agent (EDTA or citric acid). The chelating agent stabilized $Ti^{3+}$ ions in solution, allowing the reaction between $Ti^{3+}$ and $MoS_4^{2-}$ to proceed in acidic media. The optimum pH for synthesis was between 3 and 4, resulting in a nearly stoichiometric ratio of $TiO_2$ and $MoS_2$ (Table 1, Entry 1). Accordingly, another embodiment of the invention relates to a process wherein the preparation of the nanoparticles is performed under acidic conditions, preferably at pH in the range of 3 to 4, and a chelating agent selected from EDTA or citric acid is added during preparation.

TABLE 1

Properties of the as-synthesized catalysts.

| Entry | Material | Mo (wt %)[a] | S/Mo ratio[b] | Mo/Ti ratio[b] | SSA (m² g⁻¹) |
|---|---|---|---|---|---|
| 1 | $MoS_2/TiO_2$-RCP1 | 13.3 | 2.1 | 0.30 | 117 |
| 2 | Co—$MoS_2/TiO_2$-RCP1 | 13.9 | n.m. | n.m. | n.m. |
| 3 | $MoS_2/TiO_2$-RCP2-T | 5.9 | n.m. | n.m. | 96 |
| 4 | $MoS_2/TiO_2$-RCP2-H | 3.2 | 2.5 | 0.04 | 129 |

[a] Sample 1 and 4 determined by XRF, sample 2 and 3 determined by ICP-OES.
[b] molar ratio n.m. = not measured.

Synthesis and Characterization of $TiO_{2-x}$ Support

Supported catalysts were synthesized either in a single step, directly from a solution of the respective metal salts (RCP1) or from a dispersion of $TiO_{2-x}$ support precursor (wherein x has a value between 0 and 0.3, as is common practice in solid-state chemistry to define non-stoichiometric/deficient structures) in a solution of $(NH_4)_2MoS_4$ (RCP2). The $TiO_{2-x}$ support precursor was prepared prior to introduction of the $(NH_4)_2MoS_4$ salt. The advantage of this approach (RCP2) is that the morphology of the $TiO_{2-x}$ support precursor can be modified by adjusting synthesis parameters (T, pH) without affecting the redox reaction between $Ti^{3+}$ and $MoS_4^{2-}$, thus preventing unwanted side reactions.

An embodiment of the invention relates to two methods that can be employed to synthesize $TiO_{2-x}$ support precursors, being thermolysis or hydrolysis.

Accordingly, in the first method, thermolysis, $TiO_{2-x}$ was synthesized overnight from an acidic $TiCl_3$ solution at 100° C. In the second method, hydrolysis, aqueous $TiCl_3$ was hydrolyzed by adding a base (1M NaOH solution) and subsequently kept overnight at 60° C. to obtain $TiO_{2-x}$. Both methods yielded suspensions of fine blue $TiO_{2-x}$ particles, which oxidized within one hour to $TiO_2$ when exposed to air. As such, it was important to keep $TiO_{2-x}$ under inert atmosphere prior to reaction with thiomolybdate.

Figure 2A:
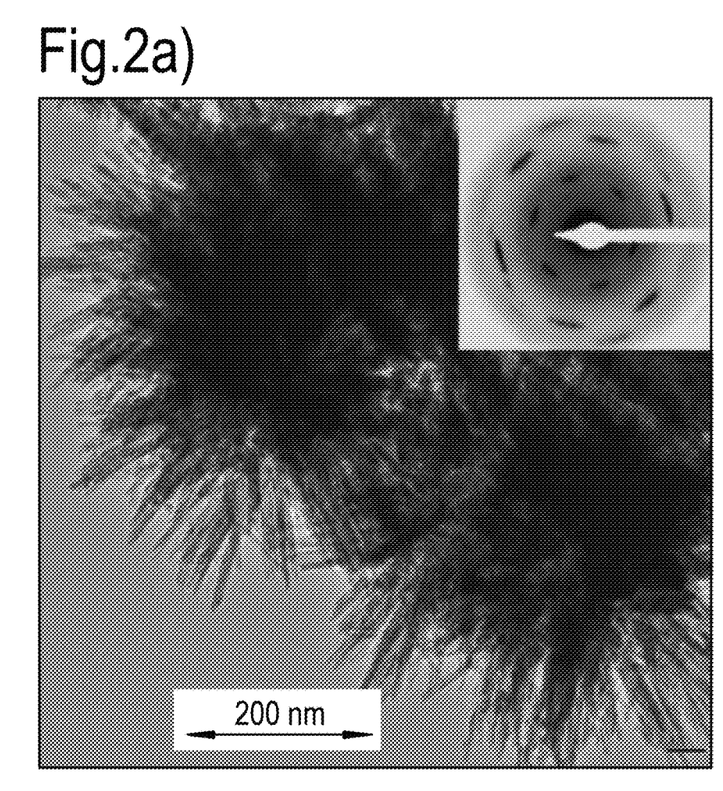
FIG. 2: TEM images of $TiO_2$ prepared by thermolysis (a) or hydrolysis (b). Inset: electron diffraction pattern.
Figure 2B:
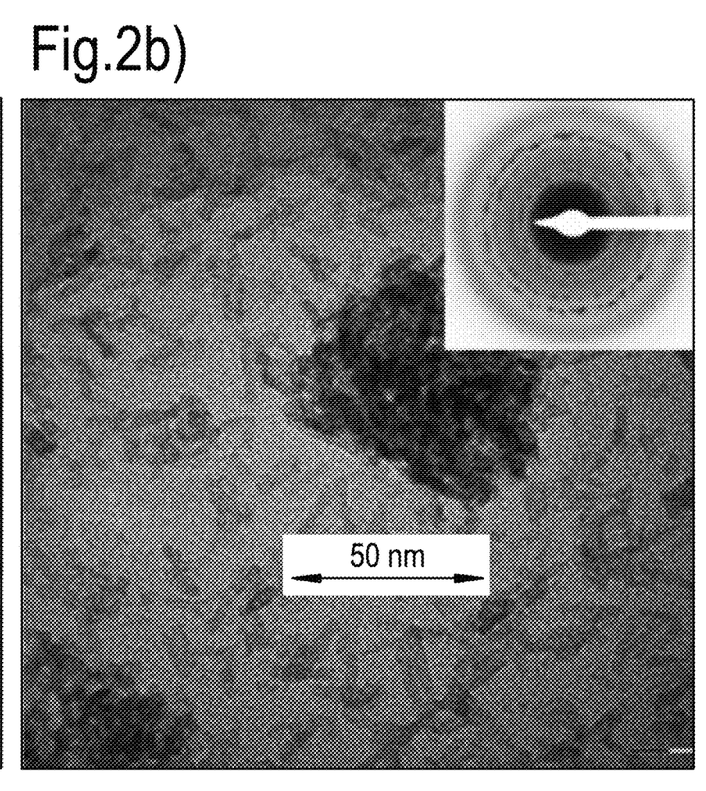
Figure 3A:
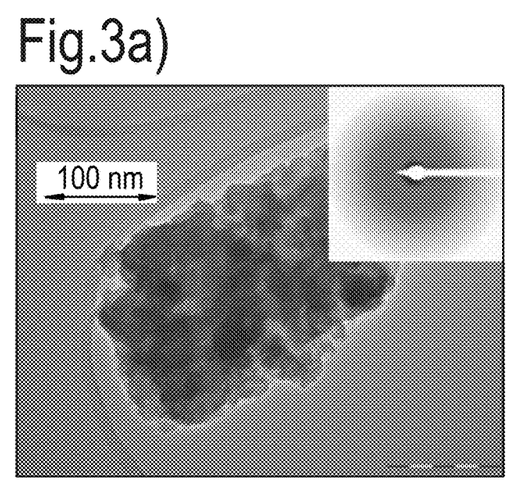
FIG. 3. TEM images of a) $MoS_2/TiO_2$ prepared by RCP1 in water. Inset: ED pattern. b) HRTEM image of the same sample. $MoS_2$ is indicated. c) $MoS_2/TiO_2$-RCP2-T. d) HRTEM picture of the same sample. The (110) crystal lattice of rutile $TiO_2$ and stacked $MoS_2$ particles are indicated.
Figure 3B:
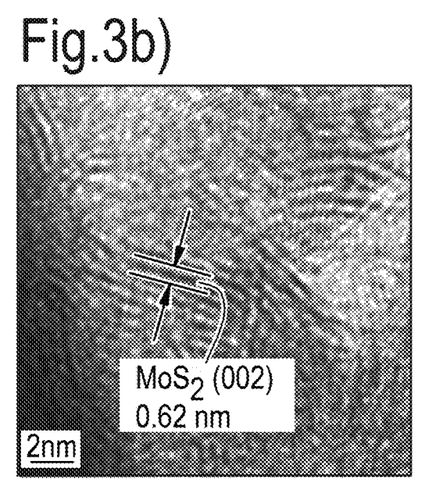
Figure 3C:
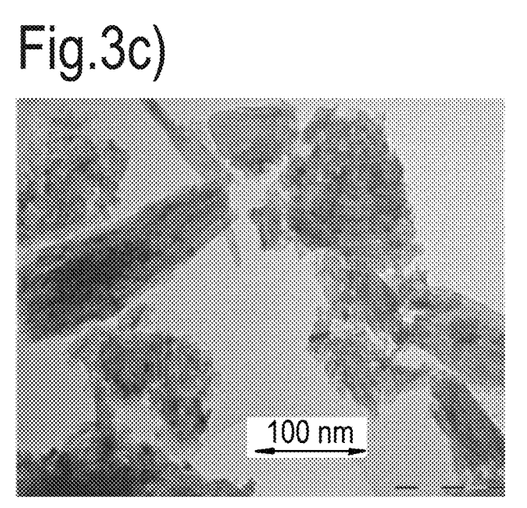
Figure 3D:
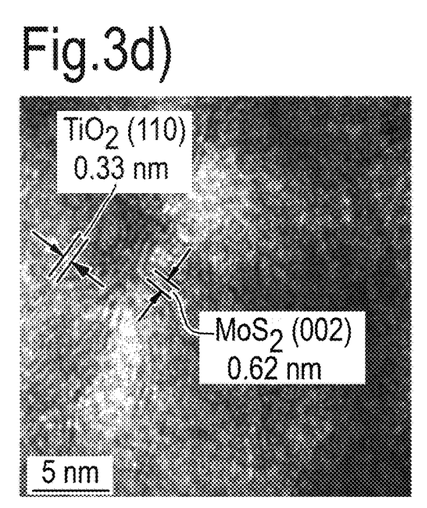
Figure 7:
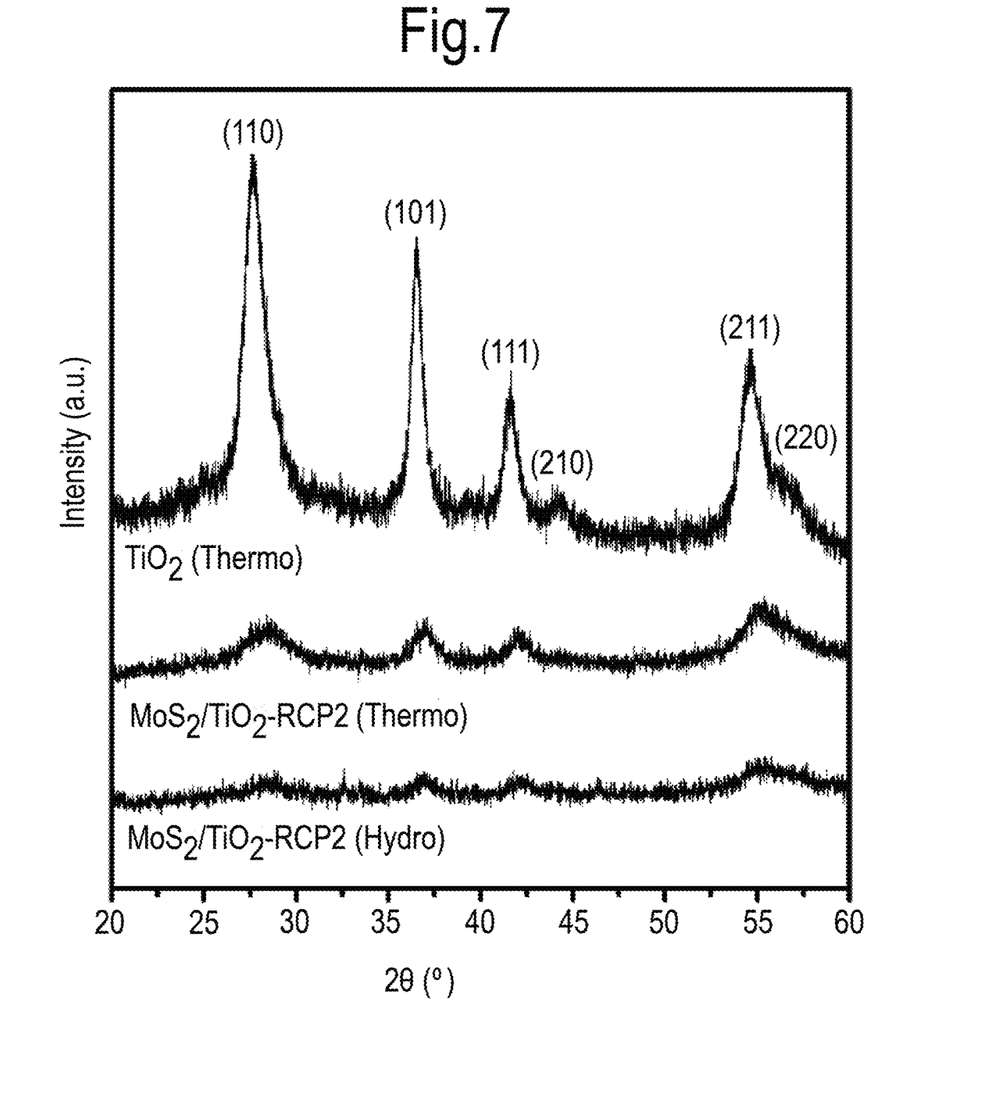
FIG. 7: X-ray diffractograms of $TiO_2$ and $MoS_2/TiO_2$ prepared by RCP2 after thermolysis or hydrolysis.

Transmission electron microscope (TEM) images of $TiO_2$ particles obtained by thermolysis and hydrolysis are shown in FIG. 2. Thermolysis yielded nanosized rods of approximately 200 nm in length that tended to form spherical aggregates. Electron diffraction (ED) confirmed that the particles were crystalline and were composed of the rutile polymorph, which was also confirmed by XRD (FIG. 7). $TiO_2$ nanoparticles obtained by hydrolysis were approximately 25 nm in length and were polycrystalline. Both rutile and brookite were identified by electron diffraction patterns, however the presence of anatase could not be excluded. Thus, the thermolysis and hydrolysis methods differ in the type of titania formed. Thermolysis gives mainly rutile and hydrolysis gives polycrystalline rutile-brookite. From a perspective of support phase control thermolysis is the preferred method.

Synthesis and Characterization of $MoS_2/TiO_2$ Catalysts

Four catalysts were prepared via the two RCP routes; their compositions are listed in Table 1. An unpromoted and Co-promoted catalyst with high Mo-loadings were prepared in a single step from aqueous solution by RCP1. The addition of Co during synthesis did not affect the redox process between $Ti^{3+}$ and $MoS_4^{2-}$ and yielded similar materials as far as the states of Ti and Mo are concerned.

Therefore, only characterization of the unpromoted catalyst samples is discussed in the following paragraphs.

For RCP2 catalysts, $TiO_{2-x}$ support precursors were synthesized either by thermolysis (RCP2-T) or hydrolysis (RCP2-H). Next, a solution of thiomolybdate was introduced, which was immediately reduced by the $TiO_{2-x}$ phase to form $MoS_2$ nanoparticles on a $TiO_2$ surface. This procedure yielded catalysts with low Mo loadings, likely due to the limited availability of $Ti^{3+}$ on the $TiO_{2-x}$ surface as indicated by the light blue color of the material. The specific surface areas (SSA) of catalysts prepared by RCP1 and RCP2 were comparable (100-130 $m^2\ g^{-1}$, Table 1). The SSA's were obtained on $MoS_2$-loaded samples, which suggests that the SSA of $TiO_2$ synthesized by RCP is substantially higher than that of a typical $TiO_2$ support (P25, SSA=50 $m^2\ g^{-1}$).

The transmission electron microscope (TEM) images in FIG. 3 show catalysts synthesized by the RCP1 and RCP2 methods. The presence of crystalline $TiO_2$ or $MoS_2$ phases in $MoS_2/TiO_2$-RCP1 could not be confirmed by electron diffraction (FIG. 3a inset), indicating that the catalyst was mainly amorphous. A high resolution TEM (HR-TEM) image of the same particle did reveal the presence of stacked $MoS_2$ layers with a characteristic d-spacing of 0.615 nm (FIG. 3b). The TEM image of $MoS_2/TiO_2$-RCP2-T (FIG. 3c) clearly shows deposits on the $TiO_2$ rods. Furthermore, the presence of $MoS_2$ in the same region was identified by HR-TEM (FIG. 3d). This suggests that both synthesis methods successfully yielded $MoS_2$. No crystalline $MoS_2$ could be detected by XRD, which may be attributed to the small particle size or disordered structure of the $MoS_2$ phase (FIG. 7).

Figure 4A:
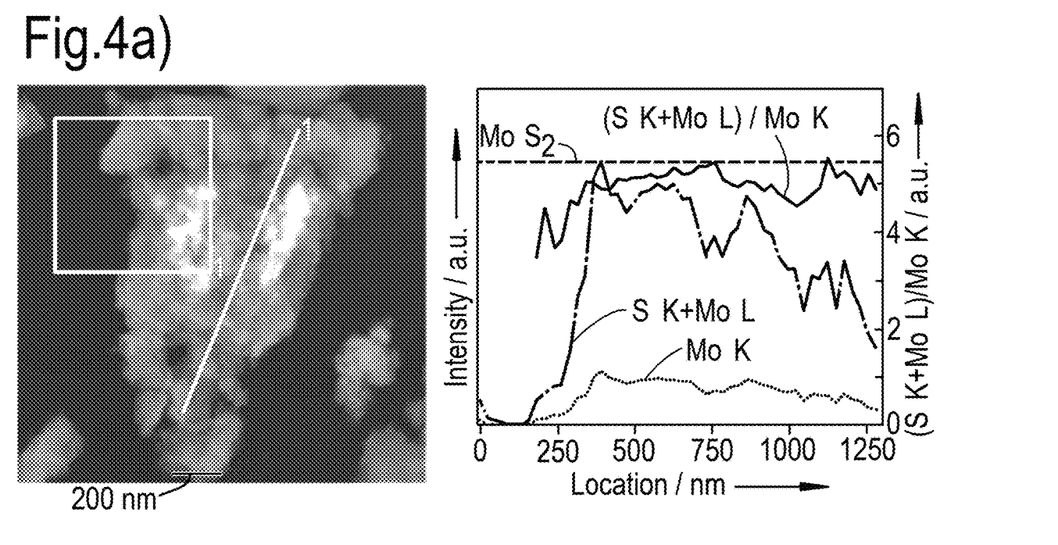
FIG. 4. TEM-EDX linescan of (a) $MoS_2/TiO_2$-RCP1 and (b) $MoS_2/TiO_2$-RCP2-T. The linescan started at 1 as indicated in the TEM image (left) and the intensities of the emission lines are plotted on the right. The black dotted line indicates the intensity ratio of (S K+Mo L)/Mo K emission lines of a bulk $MoS_2$ reference sample. According to standard terminology in electron microscopy the labels K and L refer to the electron structure of the atoms (K, L, M, . . . shells).
Figure 4B:
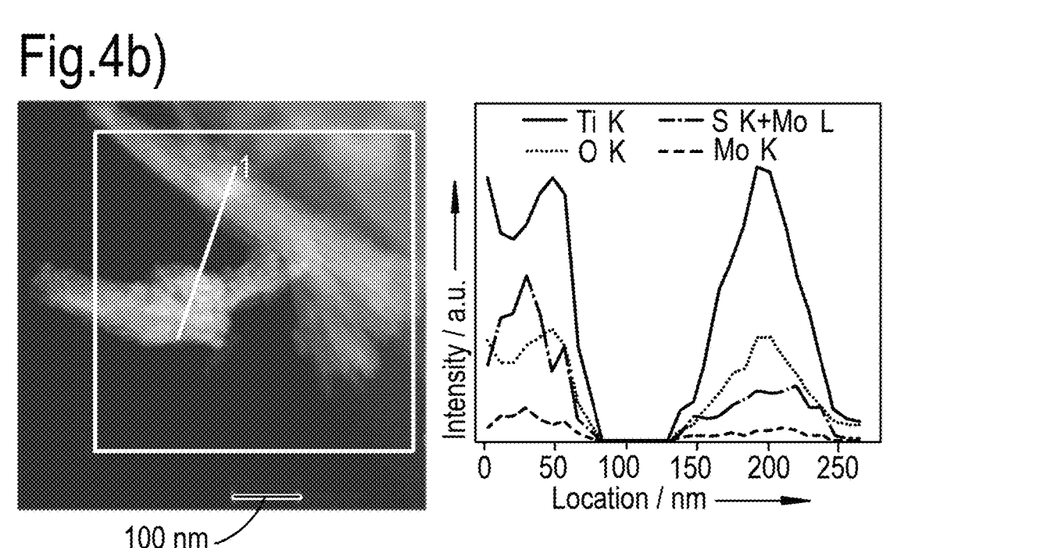

The homogeneity of $MoS_2$ on the support was evaluated by energy dispersive X-ray spectroscopy (EDX) and is shown in FIG. 4. In both samples prepared by RCP1 and RCP2, the intensity of the Mo K and Ti K fluorescence lines varied simultaneously over the length of the linescan, indicating an even loading of Mo on $TiO_2$ (FIG. 4d). The stoichiometry of S to Mo could not be determined directly by EDX since the emission lines of the S K (2307 eV) and Mo L shell (2293 eV) overlapped. Instead, the (S K+Mo L)/Mo K intensity ratio was compared to that of bulk $MoS_2$ as displayed in FIG. 4b. The obtained ratio for the samples was similar to bulk $MoS_2$, pointing to a successful reduction of thiomolybdate to $MoS_2$.

Figure 5:
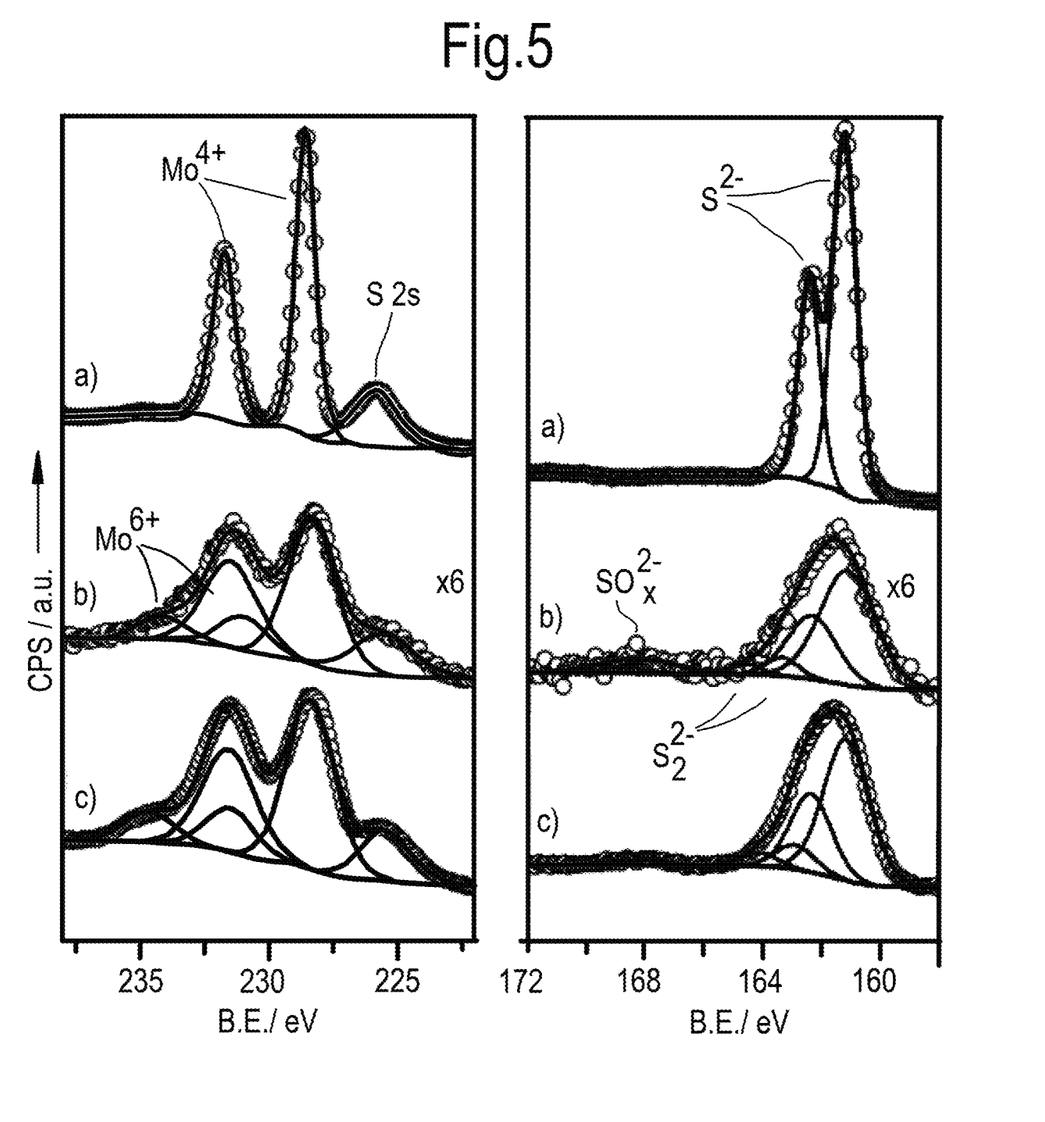
FIG. 5: Fitted Mo 3d (left) and S 2p (right) XP spectra of a) bulk $MoS_2$ reference, b) $MoS_2/TiO_2$-RCP2-T and c) $MoS_2/TiO_2$-RCP1. The datapoints are represented by open circles and the lines represent the fits. The various contributions to the fit are labeled in the graphs. The spectra of $MoS_2/TiO_2$-RCP2 were magnified six times.
Figure 8:
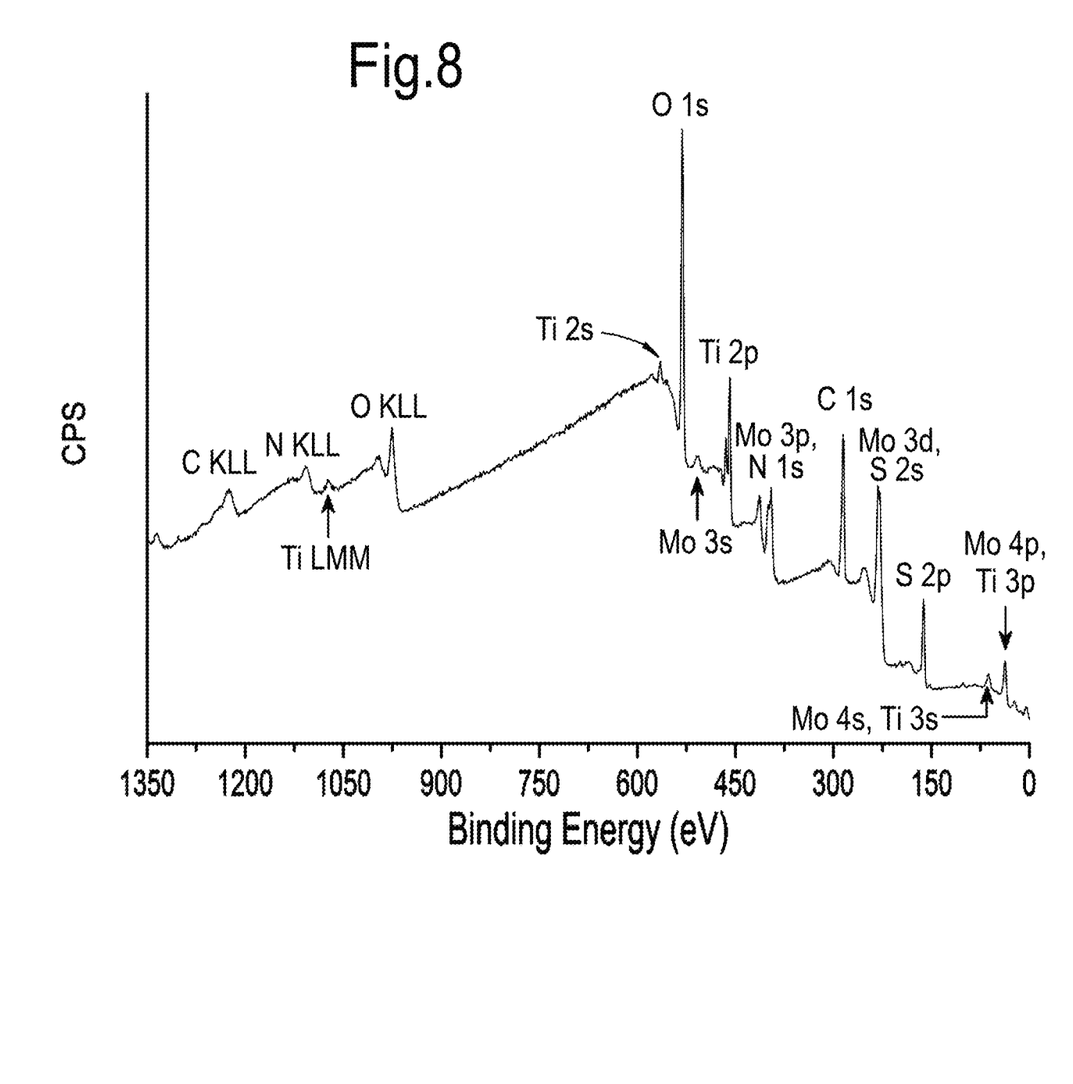
FIG. 8: XPS survey scan of sample $MoS_2/TiO_2$-RCP1.

In FIG. 5 the X-ray photoelectron spectra (XPS) of $MoS_2/TiO_2$-RCP1 and $MoS_2/TiO_2$-RCP2-T are compared with that of bulk $MoS_2$. The Mo 3d XP spectra reveal the presence of Mo in the 4+ and 6+ oxidation states. A lower binding energy (BE) was observed for the $TiO_2$ supported samples with respect to the bulk $MoS_2$ reference (Table 2). This shift in BE is attributed to electron donation from $TiO_2$ to which indicates a strong TMS-support interaction. The S 2p XP spectra are mainly composed of $S^{2-}$ and $S_2^{2-}$ species.[16] A small amount of oxidized S was also identified ($SO_x^{2-}$). This indicates that oxidized Mo and S species were likely formed by oxidation of $MoS_2$ during storage under ambient conditions. The sulfidation of Ti was not observed in the as synthesized samples. The stoichiometry of reduced sulfur to molybdenum for the samples prepared by RCP is comparable to bulk $MoS_2$ (Table 2), in line with the EDX results. A survey scan confirms that the as-synthesized catalysts are mainly composed of Mo, S, Ti and O (FIG. 8). Residual C and N species were also detected in the survey scan of the as synthesized samples. In view of the low solubility of EDTA, this is attributed to the presence of EDTA in the as-synthesized materials. Nevertheless, EDTA thermally decomposes under reaction conditions. Thus, it is not expected that it affected the catalytic properties of the materials.

TABLE 2

| | Mo 3d XPS fit results | | | |
|---|---|---|---|---|
| Sample | $Mo^{4+}$ B.E. (eV) | $Mo^{6+}$ B.E. (eV) | $Mo^{4+[a]}$ (%) | $S/Mo^{[b]}$ |
| $MoS_2/TiO_2$-RCP1 | 228.4 | 231.5 | 79 | 1.9 |
| $MoS_2/TiO_2$-RCP2-T | 228.4 | 231.2 | 81 | 2.1 |
| $MoS_2$ | 228.9 | — | 100 | 2.1 |

[a]Calculated as $I_{Mo4+}/(I_{Mo4+} + I_{Mo5+})$ where/is peak intensity.

[b]Calculated as $I_{Sred}/I_{Mo4+}$ where $S_{red}$ is the peak intensity of sulfur excluding sulfate.

Catalytic Hydrodesulfurization Properties

The catalytic activity and selectivity of samples prepared by RCP1 and RCP2 were evaluated in the liquid-phase HDS of dibenzothiophene (DBT) at 4.0 MPa and 245° C. Desulfurization of DBT can proceed via two pathways as displayed in Scheme 1. Desulfurization of DBT via hydrogenolysis (DDS) yields biphenyl as product, whereas hydrogenation of DBT followed by sulfur extraction (HYD) yields cyclohexylbenzene that can further be hydrogenated to bicyclohexane.

Scheme 1.
Simplified mechanism of the desulfurization of DBT via
direct desulfurization (DDS) or hydrogenation (HYD).

Figure 9:
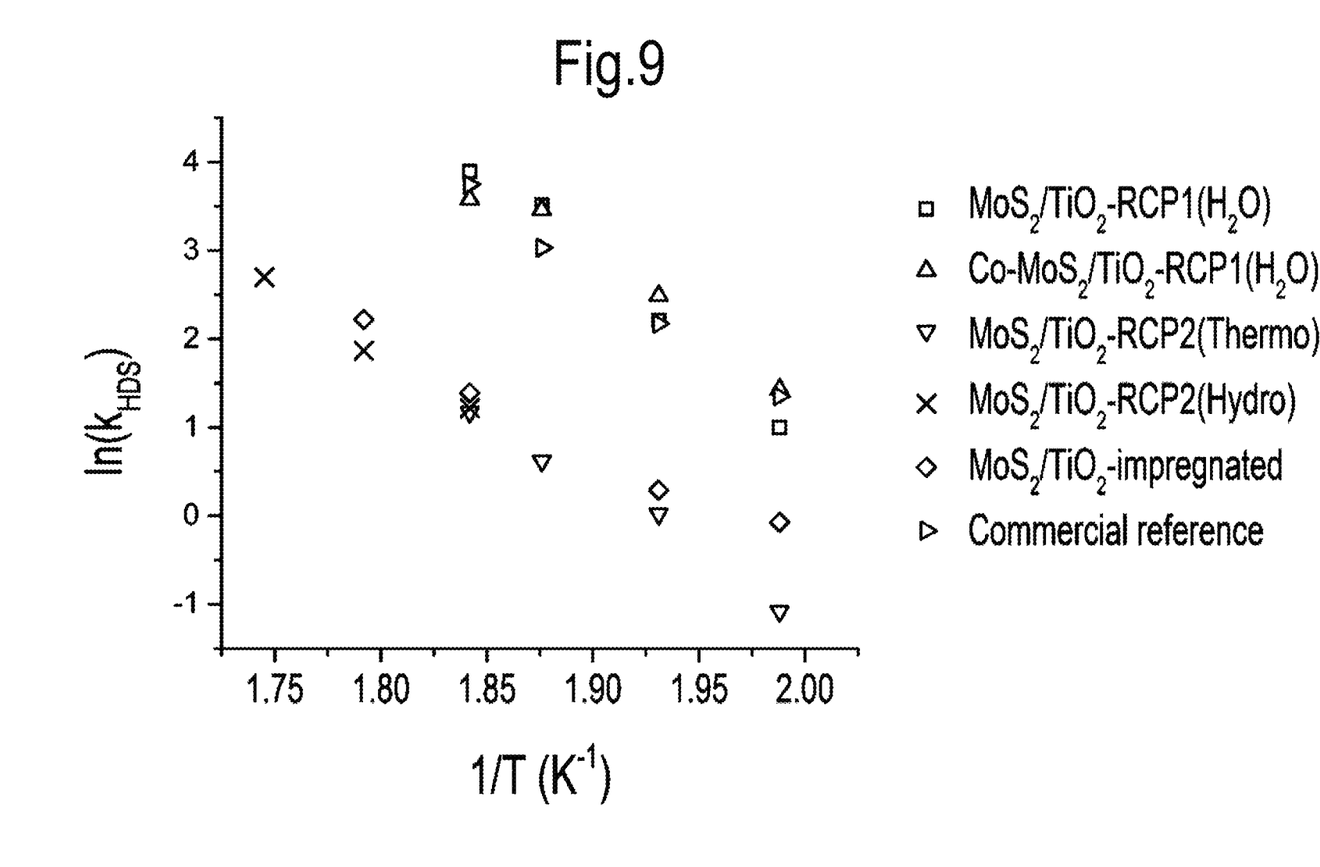
FIG. 9: Arrhenius plot obtained from the DBT activity data of RCP samples and a commercial reference.
Figure 10:
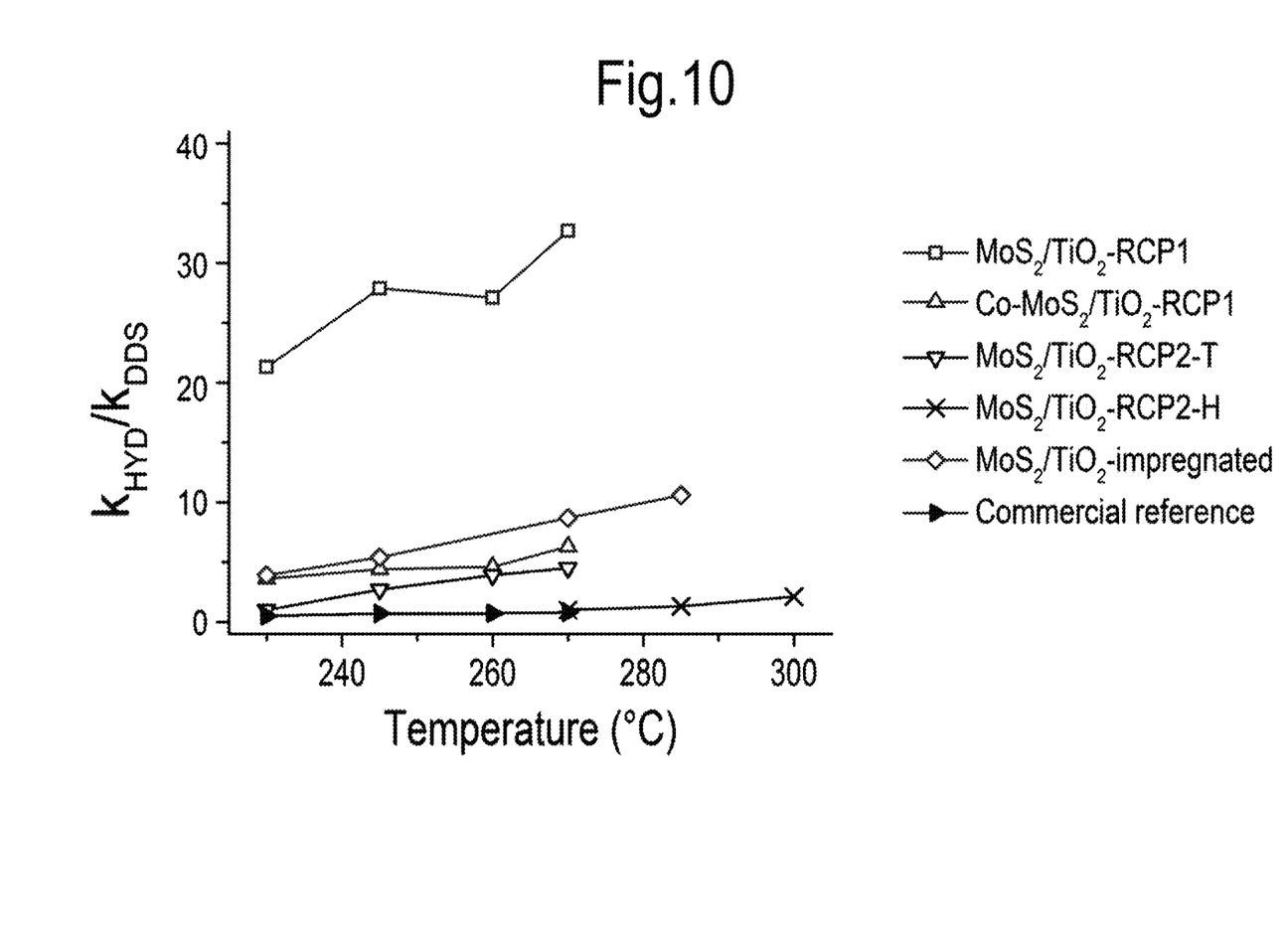
FIG. 10: Selectivity as a function of temperature. Lines connect the points and are only drawn to guide the eye.

Table 3 reports the results obtained from DBT activity tests of RCP and reference samples. Additional selectivity (FIG. 10) and Arrhenius plots (FIG. 9) are provided in the Supporting Information. The reference samples were $MoS_2$ supported on P25 titania (65% anatase, 35% rutile) and a $\gamma$-$Al_2O_3$ supported commercial Co—Mo catalyst. Highest activities were obtained for unpromoted and Co-promoted $MoS_2/TiO_2$ prepared by RCP1, which exceeded the activity of the commercial reference with comparable metal loading. Thus, another embodiment of the invention relates to the use of unpromoted and Co-promoted $MoS_2$ nanoparticles supported on titania prepared by the single step process as described herein as hydrodesulfurization catalysts. Catalysts prepared by RCP2 showed similar activity as the $MoS_2$/P25 reference, but were significantly less active than samples prepared by RCP1.

TABLE 3

Catalytic properties of the various samples in the liquid-phase HDS of DBT at 245° C. and 20 bar $H_2$.

| Sample | $k^{[a]}$ ($g_{Mo}^{-1} * hr^{-1}$) | $k_{BP}^{[b]} * 10^4$ ($mol_{BP} * mol_{Mo}^{-1} * hr^{-1}$) | HYD/DDS[c] | $E_a^{[d]}$ ($kJ * mol^{-1}$) |
|---|---|---|---|---|
| $MoS_2/TiO_2$-RCP1 | 9.1 | 0.85 | 27.9 | 170 |
| Co—$MoS_2/TiO_2$-RCP1 | 12.1 | 6.1 | 4.4 | 128 |
| $MoS_2/TiO_2$-RCP2-T | 1.0 | 0.73 | 2.7 | 124 |
| $MoS_2/TiO_2$-RCP2-H | n.m. | n.m. | n.m. | 128 |
| $MoS_2$/P25 impregnated[e] | 1.3 | 0.55 | 5.4 | 115 |
| Commercial reference[f] | 8.8 | 14.0 | 0.7 | 125 |

[a] Estimated error margin ± 10%.
[b] Rate constant for formation of biphenyl
[c] Defined as ([Products] − [BP])/[BP].
[d] Arrhenius plots are in FIG. S4. Estimated error margin ± 10%.
[e] Prepared by pore volume impregnation, Mo-loading 7.5% wt.
[f] Commercial Co—Mo/γ-$Al_2O_3$ catalyst containing approx. 15% wt Mo.

The high activity of $MoS_2/TiO_2$-RCP1, as compared with the commercial catalyst, is remarkable since it does not contain a promoter. The sample was about eight times more active than $MoS_2/TiO_2$ prepared by impregnation or RCP2. However, the production rate constant of biphenyl (BP) was similar for all unpromoted samples supported on $TiO_2$. The high activity obtained by the RCP1 method can thus be attributed to increased hydrogenation activity. The higher apparent activation energy of $MoS_2/TiO_2$-RCP1 points to a different formation mechanism of this sample compared to the others. When Co was present in the catalyst (Co—$MoS_2$/$TiO_2$-RCP1), the selectivity towards BP increased drastically while the overall rate only increased by 30%. The Mo-loading remained constant, indicating that active HYD sites were replaced by DDS sites.

Several researchers have reported an increased hydrogenation activity of $MoS_2$ catalysts supported on $TiO_2$ versus those on other support materials.[11b,17] It has been proposed that $Ti^{3+}$, which may form under the reducing HDS conditions, could act as an electronic promoter in hydrogenation reactions over Ti—S—Mo sites.[17, 18] The present results agree with this proposition, as addition of Co led to increased DDS activity at the expense of HYD activity. This suggests that Co resides at $MoS_2$ edge sites that would otherwise be promoted by Ti. Consequently, Co-promotion in $MoS_2/TiO_2$ catalysts does not increase the overall HDS rate to the same extent as it does in γ-$Al_2O_3$ supported catalysts.[9c, 17]

Despite the similar textural properties of catalysts prepared by RCP1 and RCP2, their morphologies as observed by TEM were obviously different. RCP2 and impregnated samples, which exhibited a relatively low hydrogenation activity, were prepared by depositing $MoS_2$ on a well-defined $TiO_2$ support. On the other hand, catalysts prepared by RCP1 were composed of co-precipitated $MoS_2$ and amorphous $TiO_2$. It is anticipated that the RCP1 method yielded more Ti-promoted sites that are active in hydrogenation, which may explain the increased hydrogenation activity of these materials. Further studies in our laboratory aim to characterize the amorphous $TiO_2$ support and explore the unique activity of $MoS_2/TiO_2$-RCP catalysts in ultra-deep HDS applications with real feed.

Conclusions

Unpromoted and cobalt-promoted molybdenum disulfide nanoparticles supported on titania were synthesized from aqueous solutions containing Ti and Mo precursor salts by an in situ redox reaction. The synthesis method, reductive co-precipitation (RCP), is simple and proceeds under mild conditions. Moreover, catalysts prepared via this way have higher Mo-loading than those prepared via impregnation and are comparable with commercial catalysts. Analysis by EDX indicated that the samples were composed of homogeneously dispersed $MoS_2$ nanoparticles on amorphous $TiO_2$. The morphology of $TiO_2$ could be controlled by synthesis of $TiO_{2-x}$ prior to $MoS_2$ deposition, but this was at the expense of a lower Mo loading. Highest activities were obtained for promoted RCP1 samples, which exceeded the performance of a commercial reference in DBT HDS. Thus, an embodiment of the invention relates to the use of Co-promoted $MoS_2$ nanoparticles supported on titania prepared by the single step process as described herein as hydrodesulfurization catalysts. The addition of Co as promoter did not enhance the catalytic activity of $MoS_2/TiO_2$ to the same extend (+30%) as for $Al_2O_3$-supported Co—Mo catalysts. However, the promoter did change the selectivity towards hydrogenolysis products at the expense of hydrogenation products. This points to the substitution of Ti-promoted sites by Co-promoted sites upon addition of Co.

The invention is illustrated by the following non-limiting examples.

EXAMPLES

Materials Preparation

A detailed description of the materials synthesis is provided in the Supporting Information (vide infra). Key aspects of the materials synthesis are given below. The RCP synthesis procedure was modified from Xie et al.[5a] $MoS_2/TiO_2$-RCP1 was synthesized from aqueous solutions of $TiCl_3$ and $(NH_4)_2MoS_4$ at 100° C. The promoted material, Co—$MoS_2/TiO_2$-RCP1, was synthesized via the same procedure with $Co(NO_3)_2.6H_2O$ added to the $TiCl_3$ solution. For the preparation of RCP2 materials, $TiO_{2-x}$ was synthesized first by thermolysis (T) or hydrolysis (H). In thermolysis, $TiO_{2-x}$ was formed overnight at 60° C. from an aqueous solution of $TiCl_3$ in HCl, stabilized by NaCl. In hydrolysis, $TiO_{2-x}$ was formed overnight at 60° C. by basification of acidic $TiCl_3$ solution with NaOH (1M). $TiO_{2-x}$ was filtered and washed and redispersed in water. $MoS_2/TiO_2$-RCP2 materials were then synthesized by addition of an aqueous $(NH_4)_2MoS_4$ solution to the suspension of $TiO_{2-x}$ under inert conditions.

Characterization $N_2$ adsorption isotherms were measured at −196° C. on a Micromeretics Tristar II. Prior to analysis, samples were heated at 160° C. for 4 hr under flowing $N_2$. Specific surface area was determined by the BET method. Transmission Electron Microscopy measurements were made with a Tecnai-20F microscope operated at 200 kV and equipped with a field-emission gun. The elemental analysis by energy-dispersive X-ray spectroscopy was performed on the same microscope, utilizing an EDAX analyzer with TIA software. X-ray diffraction (XRD) patterns were recorded with a PANalytical X'pert PRO powder diffractometer equipped with a sealed Cu anode tube, operated at 45 kV and 40 mA. Samples were ground with a mortar and pestle prior to analysis. X-ray photoelectron spectroscopy (XPS) was performed with a Kratos AXIS Ultra spectrometer, equipped with a monochromatic X-ray source and a delay-line detector (DLD). Spectra were obtained using the aluminium anode (Al Kα=1486.6 eV). Survey scans were measured at a constant pass energy of 160 eV and region scans at 40 eV. The background pressure was $2 \times 10^{-9}$ mbar. Energy correction was performed by using the C 1s peak at 284.6 eV as a reference. X-ray fluorescence (XRF) was recorded with a PANalytical spectrometer equipped with a MagiX Pro (PW2440). Samples were mixed with $Al_2O_3$ and a glass bead was sintered for analysis.

Catalytic Hydrodesulfurization Activity

The catalytic activity was determined by means of dibenzothiophene (DBT) hydrodesulfurization in a fixed bed high-pressure tubular reactor with a down-flow (trickle flow) of gas and liquid feed (40 bar, $H_2$ flow of 2.25 ml min$^{-1}$, WHSV of 1.4 h$^{-1}$). The reactor, 240 mm in length and 4 mm in diameter (ID) was packed with 400 mg of 30 to 80 mesh catalyst particles sandwiched between two $ZrO_2$ layers. The catalysts were pretreated with n-hexadecane (Sigma-Aldrich) spiked with 5.2% tetranonyl pentasulfide (TNPS, Sigma-Aldrich) at 280° C. for 5 hours and subsequently at 340° C. for 24 hours. Afterwards, the temperature was lowered to 200° C. for 8 hours. Then, the feed was switched to the reaction feed (5 wt. % DBT, 2 wt. % adamantane in n-hexadecane). After equilibration for 2 hours, the temperature was increased to the desired reaction temperature (245° C.). Steady-state activity was measured after 24 hours of reaction by offline GC-FID.

Supporting Information

1. Experimental Details

Catalysts were prepared by one-step RCP or two-step RCP. To prevent oxidation of Ti(III) by air, all solutions were prepared in a glovebag (purged 3 times with oxygen-free $N_2$ gas) from demineralized and degassed water.

1.1 One-Step Reductive Co-Precipitation

In a typical one-step RCP experiment, 1 g (3.8 mmol) ammonium tetrathiomolybdate (ATM, Sigma-Aldrich) was dissolved in 40 ml water and 10 ml ammonia (25%, Sigma-Aldrich) and filtered to remove residual particles (pH 11). A Ti[EDTA] solution was prepared by dissolving 2.48 g (7.6 mmol) ethylendiaminetetraacetic acid diammonium hydrate salt (EDTA, Sigma-Aldrich) in 30 ml water, adding 7.6 ml (7.6 mmol) titanium trichloride in hydrochloric acid (2-3M) solution (Sigma-Aldrich) and 2.1 ml concentrated ammonia. For promoted samples, 30 ml aqueous solution of cobalt nitrate hexahydrate (1.7 mmol, Sigma-Aldrich) was slowly poured into the dark-purple $TiCl_3$ solution. The obtained Ti[EDTA] solution (pH 1) was added dropwise to the ATM solution. The reaction mixture was refluxed for 24 hours at 100° C. A black suspension was formed, which was centrifuged and washed with water. The black residue was dried in nitrogen atmosphere at 50° C. A black solid was obtained.

1.2 Two-Step Reductive Co-Precipitation

In a typical two-step RCP experiment, 1 g (3.8 mmol) ATM was dissolved in 50 ml 0.2M citric acid or EDTA solution and subsequently filtered to remove residual particles. The pH was adjusted to 11 by adding concentrated ammonia (25%). The ATM solution was added to a blue suspension of reduced titanium oxide ($TiO_{2-x}$) in water prepared either via thermolysis or hydrolysis. The suspension was refluxed for 16 hours at 60° C. A dark brown suspension was formed, which was centrifuged and washed with water. The brown residue was dried in nitrogen atmosphere at 50° C. A dark brown solid was obtained.

1.3 Preparation of Blue Titania

Blue titania was prepared by thermolysis (see Y. Xie, K. Ding, Z. Liu, R. Tao, Z. Sun, H. Zhang, G. An, *J. Am. Chem. Soc.* 2009, 131, 6648-6649) or hydrolysis.

Thermolysis: 10 g of an aqueous solution of $TiCl_3$ (20%) and hydrochloric acid (3%) (Alpha Aesar) was added to 26 g of an aqueous solution of NaCl (30%) (Sigma-Aldrich). A purple solution was obtained. After refluxing for 16 hours at 100° C. under nitrogen atmosphere a blue suspension was obtained, which was filtered, washed and redispersed in water.

Hydrolysis: 5.9 g of a solution of $TiCl_3$ (20%) in hydrochloric acid (3%) solution was dissolved in 45 ml water. Subsequently, 24 ml 1 M NaOH (Sigma-Aldrich) were slowly added and the solution turned black. After refluxing at 60° C. in nitrogen atmosphere for 16 hours a blue suspension was obtained with a pH of 1. The solution was neutralized by adding 1 M NaOH.

1.4 Preparation of Ti[NTA] Solution 11.6 g nitrilotriacetic acid (NTA) were suspended in 60 ml water. The pH was adjusted to 9 with concentrated ammonia solution (25%) and the solution became clear. Subsequently, 11.6 ml of an aqueous solution of $TiCl_3$ (20%) and HCl (3%) were added dropwise and under vigorous stirring to the NTA solution. The solution turned green.

During the addition of $TiCl_3$ it is important to maintain the pH of the solution to above 2 to prevent precipitation. The pH was increased by adding a saturated $(NH_4)_2CO_3 \cdot NH_4HCO_3$ solution (do not use ammonia to increase the pH since it will precipitate $Ti^{3+}$). When all the $TiCl_3$ was added to the solution, the pH was adjusted to 7 with saturated $(NH_4)_2CO_3 \cdot NH_4HCO_3$ solution and the volume was adjusted to 100 ml with water. A dark blue/green solution was obtained with a concentration of 0.1M Ti and 0.4M NTA.

1.4 $Mo^{6+}$—$Ti^{3+}$ Redox Reaction in Aqueous Solution

In a typical experiment, 76 ml Ti[NTA] solution were added via a septum to a round-bottom flask under nitrogen atmosphere. Meanwhile 1 g of ATM was dissolved in 50 ml 0.2M citric acid solution. The solution (pH 7) was stirred at room temperature for one hour and then filtered under nitrogen atmosphere to remove residual particles. A dark-red solution was obtained and added to the dark blue Ti[NTA] solution via a septum. A black precipitate was immediately formed and the pH dropped to 6.5. The suspension was refluxed for 4 hours at 60° C. The pH increased to 7-7.5. The black suspension was centrifuged and washed with water. The black residue was dried in nitrogen atmosphere at 50° C. A fine black powder was obtained.

2. Redox Reaction Between $Mo^{6+}$ and $Ti^{3+}$ in Aqueous Solution.

To investigate the redox reaction between $Ti^{3+}$ and $Mo^{6+}$, it is important to exclude any pH effects that can lead to undesired precipitation of side products. Neutral solutions of $Ti^{3+}$ and $MoS_4^{2-}$ were prepared by chelation according to the procedure described in section 1. When the Ti[NTA] solution was added to the ATM solution at room temperature, a black precipitate formed instantly, indicating that the redox reaction between $Ti^{3+}$ and $MoS_4^{2-}$ is fast.

Chemical analysis by XRF (sample 6, Table S1) reveals that the product consists of $MoS_2$ particles with a nearly stoichiometric ratio of S to Mo. Titanium does not precipitate from solution as only trace amounts of titanium were detected in the sample. The TEM pictures (FIG. 6) show that the particles are rather large (~200 nm) and are composed of amorphous $MoS_2$. Layered structures are visible in the HR-TEM image; the distance between planes is characteristic of the interlayer distance in stacked $MoS_2$ particles along the [001] direction. The negligible presence of titanium in the sample can be rationalized by chelation of $Ti^{4+}$ with NTA, which form stable complexes under reaction conditions. Thus, $Ti^{III}$[NTA] is oxidized to $Ti^{IV}$[NTA], which remains stable in solution. Simultaneously $Mo^{VI}S_4^{2-}$ is reduced to $Mo^{IV}S_2$, which is insoluble and immediately precipitates to form the black suspension.

LIST OF REFERENCES

[1] *Preparation of solid catalysts*, Wiley-VCH, Weinheim, Germany, 1999.

[2] *Synthesis of solid catalysts*, Wiley-VCH, Weinheim, 2009.

[3] a) N. Zheng, G. D. Stucky, *J Am Chem Soc* 2006, 128, 14278-14280; b) J. Blanco, A. L. Petre, M. Yates, M. P. Martin, S. Suarez, J. A. Martin, *Adv. Mater.* 2006, 18, 1162-1165; c) R. J. White, R. Luque, V. L. Budarin, J. H. Clark, D. J. Macquarrie, *Chem Soc Rev* 2009, 38, 481-494.

[4] a) Z. C. Wang, Y. J. Jiang, R. Rachwalik, Z. W. Liu, J. Shi, M. Hunger, J. Huang, *Chemcatchem* 2013, 5, 3889-3896; b) C. Sprung, B. Arnstad, U. Olsbye, *ChemCatChem* 2014, 6, 1969-1982; c) J. M. Campelo, D. Luna, R. Luque, J. M. Marinas, A. A. Romero, *Chemsuschem* 2009, 2, 18-45.

[5] a) Y. Xie, K. Ding, Z. Liu, R. Tao, Z. Sun, H. Zhang, G. An, *J. Am. Chem. Soc.* 2009, 131, 6648-6649; b) S. Golunski, R. Rajaram, N. Hodge, G. J. Hutchings, C. J. Kiely, *Catalysis Today* 2002, 72, 107-113.

TABLE S1 description and composition of the various samples prepared via different synthesis procedures.

| Sample | Procedure | Ti precursor | Mo (wt %)[a] | S/Mo Ratio[b] | Mo/Ti Ratio[b] |
|---|---|---|---|---|---|
| 1. $MoS_2/TiO_2$-RCP1 | 1-step RCP | $TiCl_3$ | 13.3 | 2.1 | 0.30 |
| 2. Co—$MoS_2/TiO_2$-RCP1 | 1-step RCP | $TiCl_3$ | 13.9 | n.m. | n.m. |
| 3. $MoS_2/TiO_2$-RCP2-T | 2-step RCP | $TiO_{2-x}$ thermolysis | 5.9 | n.m. | n.m. |
| 4. $MoS_2/TiO_2$-RCP2-H | 2-step RCP | $TiO_{2-x}$ hydrolysis | 3.2 | 2.5 | 0.04 |
| 5. $MoS_2$-sol | Solution redox | $Ti^{III}$ [NTA] | 43.2 | 2.0 | 59.9 |

[a]Sample 1, 4 and 5 determined by XRF, sample 2 and 3 determined by ICP-OES.
[b]Molar ratio determined by XRF.

[6] W. Ho, J. C. Yu, J. Lin, J. Yu, P. Li, *Langmuir* 2004, 20, 5865-5869.

[7] M. Chhowalla, H. S. Shin, G. Eda, L. J. Li, K. P. Loh, H. Zhang, *Nat Chem* 2013, 5, 263-275.

[8] R. Prins, in *Handbook of Heterogeneous Catalysis*, Vol. 6 (Eds.: G. Ertl, H. Knozinger, F. Schuth, J. Weitkamp), 2008, pp. 2696-2718.

[9] a) M. Breysse, C. Geantet, P. Afanasiev, J. Blanchard, M. Vrinat, *Catal Today* 2008, 130, 3-13; b) K. Y. S. Ng, E. Gulari, *J. Cat.* 1985, 92; c) J. Ramirez, S. Fuentes, G. Diaz, M. Vrinat, M. Breysse, M. Lacroix, *Applied Catalysis* 1989, 52, 211-224.

[10] a) S. Dzwigaj, C. Louis, A. Breysse, M. Cattenot, V. Belliere, C. Geantet, M. Vrinat, P. Blanchard, E. Payen, S. Inoue, H. Kudo, Y. Yoshimura, *Applied Catalysis B: Environmental* 2003, 41, 181-191; b) J. A. Toledo-Antonio, M. A. Cortes-Jacome, C. Angeles-Chavez, J. Escobar, *Appl Catal B-Environ* 2009, 90, 213-223.

[11] a) A. Guevara, A. Alvarez, M. Vrinat, *Catalysis Letters* 2008, 126, 268-274; b) M. C. Barrera, J. Escobar, C. Marin, M. Viniegra, J. A. D. L. Reyes, J. G. Pacheco, F. Murrieta, *Petroleum Science and Technology* 2004, 22, 87-101; c) Z. L. Zhang, Y. S. Zhou, S. J. Zhang, C. M. Xu, *Energy & Fuels* 2006, 20, 2293-2298; dW. Q. Huang, A. J. Duan, Z. Zhao, G. F. Wan, G. Y. Jiang, T. Dou, K. H. Chung, J. Liu, *Catalysis Today* 2008, 131, 314-321.

[12] Z. B. Wei, W. H. Yan, H. Zhang, T. L. Ren, Q. Xin, Z. C. Li, *Appl Catal a-Gen* 1998, 167, 39-48.

[13] D. L. Nguyen, S. Gillot, D. O. Souza, P. Blanchard, L. Chamonier, E. Berner, T. V. Kotbagi, M. K. Dongare, S. M. Umbarkar, S. Cristol, E. Payen, C. Lancelot, *ChemCatChem* 2012, 4, 2112-2120.

[14] a) A. Di Paola, G. Cufalo, M. Addamo, M. Bellardita, R. Campostrini, M. Ischia, R. Ceccato, L. Palmisano, *Colloid Surface A* 2008, 317, 366-376; b) S. Cassaignon, M. Koelsch, J.-P. Jolivet, *Journal of Physics and Chemistry of Solids* 2007, 68, 695-700; c) T. H. Wang, A. M. Navarrete-Lopez, S. G. Li, D. A. Dixon, J. L. Gole, *Journal of Physical Chemistry A* 2010, 114, 7561-7570.

[15] a) T. Weber, J. C. Muijsers, J. W. Niemantsverdriet, *J. Phys. Chem.* 1995, 99, 9194-9200; b) P. Afanasiev, G. F. Xia, G. Berhault, B. Jouguet, M. Lacroix, *Chem Mater* 1999, 11, 3216-3219.

[16] J. C. Muijsers, T. Weber, R. M. v. Hardeveld, H. W. Zandbergen, J. W. Niemantsverdriet, *J. Catal.* 1995, 157, 698-705.

[17] L. Coulier, J. A. R. v. Veen, J. W. Niemantsverdriet, *Catalysis Letters* 2002, 79, 149-155.

[18] J. Ramirez, G. Macias, L. Cedeno, A. Gutierrez-Alejandre, R. Cuevas, P. Castillo, *Catalysis Today* 2004, 98, 19-30.

That which is claimed is:

1. A two-step hydrolysis process for the preparation of nanoparticles of $MoS_2$ supported on $TiO_2$, wherein the two-step process comprises: preparing a dispersion of blue $TiO_{2-X}$ support particles by adding a base to an aqueous solution of $TiCl_3$ and maintaining a resulting mixture under hydrolysis conditions for a time period; keeping said dispersion under an inert atmosphere, and introducing an aqueous solution of thiomolybdate to said dispersion to form said nanoparticles; and recovering said nanoparticles that are polycrystalline rutile and brooktie.

2. A two-step process as recited in claim 1, wherein said nanoparticles have a specific surface area in the range of from 100 to 130 $m^2/g$.

3. A two-step process as recited in claim 1, wherein the value of X of the formula $TiO_{2-X}$ is between 0 and 0.3.

4. A two-step process as recited in claim 1, wherein said thiomolybdate is ammonium tetrathiomolybdate $[(NH_4)_2MoS_4]$.

5. A two-step process as recited in claim 1, wherein said nanoparticles comprise polycrystalline rutile-brookite.

6. A two-step hydrolysis process as recited in claim 1, wherein said base is sodium hydroxide.

7. A two-step thermolysis process as recited in claim 1, wherein said aqueous solution of thiomolybdate comprises ammonium tetrathiomolybdate dissolved in citric acid solution and added ammonia.

8. A hydrodesulfurization process, comprising: passing a reaction feed over a hydrodesulfurization catalyst comprising nanoparticles produced by the two-step process of claim 1.

9. A two-step thermolysis process for the preparation of nanoparticles of $MoS_2$ supported on $TiO_2$, wherein said two-step process comprises:
preparing a dispersion of blue $TiO_{2-X}$ support particles by maintaining an acidic aqueous solution of $TiCl_3$ under thermolysis conditions for a time period;
maintaining said dispersion under an inert atmosphere, and introducing an aqueous solution of thiomolybdate to said dispersion to form said nanoparticles; and
recovering said nanoparticles that are crystalline and comprises rutile polymorph.

10. A two-step process as recited in claim 9, wherein said nanoparticles have a specific surface area in the range of from 100 to 130 $m^2/g$.

11. A two-step process as recited in claim 9, wherein the value of X of the formula $TO_{2-X}$ is between 0 and 0.3.

12. A two-step process as recited in claim 9, wherein said thiomolybdate is ammonium tetrathiomolybdate $[(NH_4)_2MoS_4]$.

13. A two-step thermolysis process as recited in claim 9, wherein said acidic aqueous solution of $TiCl_3$ includes hydrochloric acid.

14. A two-step thermolysis process as recited in claim 9, wherein said aqueous solution of thiomolybdate comprises ammonium tetrathiomolybdate dissolved in citric acid solution and added ammonia.

* * * * *